US005487831A

United States Patent [19]
Pirkle et al.

[11] Patent Number: 5,487,831
[45] Date of Patent: Jan. 30, 1996

[54] RECOGNITION AND SEPARATION OF CARBON CLUSTERS

[75] Inventors: William H. Pirkle, Champaign; Christopher J. Welch, Northbrook, both of Ill.

[73] Assignee: Research Corporation Technologies, Inc., Tucson, Ariz.

[21] Appl. No.: 216,758

[22] Filed: Mar. 23, 1994

Related U.S. Application Data

[63] Continuation of Ser. No. 874,791, Apr. 27, 1992, Pat. No. 5,338,529.

[51] Int. Cl.⁶ .................................................. B01D 15/08
[52] U.S. Cl. ........................... 210/198.2; 210/321.72; 210/500.28; 210/502.1; 210/635; 210/638; 210/643; 210/644; 210/656; 502/401; 556/400
[58] Field of Search ........................ 210/635, 638, 210/643, 644, 656, 198.2, 321.72, 500.28, 500.38, 502.1; 556/400; 502/401, 402, 404; 423/445, 445 B, 460, 461

[56] References Cited

U.S. PATENT DOCUMENTS

| | | | |
|---|---|---|---|
| 4,322,310 | 3/1982 | House | 210/635 |
| 4,330,440 | 5/1982 | Ayers | 210/635 |
| 4,512,898 | 4/1985 | Oi | 210/656 |

(List continued on next page.)

FOREIGN PATENT DOCUMENTS

0299793A2  1/1989  European Pat. Off. ............ 210/198.2

OTHER PUBLICATIONS

Ajie, et al. (1990) "Characterization of the Soluble All Carbon Molecules $C_{60}$ and $C_{70}$", *Journ. Phys. Chem.* 94, 8630–8633.

(List continued on next page.)

Primary Examiner—Ernest G. Therkorn
Attorney, Agent, or Firm—Scully, Scott, Murphy and Presser

[57] ABSTRACT

Carbon clusters, such as $C_{60}$ and $C_{70}$ fullerenes are separated by means of a recognition selector having the formula:

$$R_1 - \underset{\underset{R_1}{|}}{\overset{\overset{R_1}{|}}{C}} - (CH_2)_m - W$$

wherein $R_1$ is $$-(CH_2)_n-(R_2)-(CH_2)_o-(\overset{\overset{O}{\|}}{C})_p-$$

$$(CHR_3)_q - (R_4)_r - (\overset{\overset{O}{\|}}{C})_s - (CHR_5)_t - Ar$$

wherein
$R_2$ is O, S or $NR_{12}$ wherein $R_{12}$ is independently hydrogen or P=O with the proviso that when $R_{12}$ is P=O, then only one such group is present and all $R_2$'s are additionally bonded to $R_{12}$, $R_4$ is independently O, S or NH, $R_3$ and $R_5$ are each independently hydrogen or lower alkyl, n and o are each independently zero, 1, 2 or 3, p, q, r, s and t are each independently zero or 1, Ar is a monocyclic or ortho-fused polycyclic aromatic moiety having up to 10 carbon atoms, either of which may be unsubstituted or substituted with one or more lower alkyl, $NO_2$, $N(R_6)_3^{30}$, CN COOR$_7$, $SO_3H$, $COR_8$ and $OR_9$ wherein $R_6$, $R_7$, $R_8$ and $R_9$ are each independently hydrogen or lower alkyl;

W is H or CH=CH$_2$; and m is 1 to 10.

29 Claims, 4 Drawing Sheets

U.S. PATENT DOCUMENTS

| | | | |
|---|---|---|---|
| 4,565,877 | 1/1986 | Wada | 210/656 |
| 4,604,207 | 8/1986 | Oi | 210/656 |
| 4,627,919 | 12/1986 | Yuki | 210/198.2 |
| 4,830,921 | 5/1989 | Kitayama | 210/198.2 |
| 4,919,803 | 4/1990 | Doyle | 210/198.2 |
| 4,963,254 | 10/1990 | Oi | 210/198.2 |
| 5,051,176 | 9/1991 | Miyano | 210/198.2 |
| 5,080,795 | 1/1992 | Pirkle | 210/643 |
| 5,149,426 | 9/1992 | Watabe | 210/198.2 |
| 5,318,848 | 6/1994 | Itoh | 210/198.2 |
| 5,338,454 | 8/1994 | Duff | 210/198.2 |
| 5,387,338 | 2/1995 | Pirkle | 210/198.2 |
| 5,422,004 | 6/1995 | Pirkle | 210/198.2 |

OTHER PUBLICATIONS

Atwood, et al. (1991) "X–Ray Diffraction Evidence for Aromatic π–Hydrogen Bonding of Water", *Nature* 349, 683–684.

Baum (1990) "Simple Synthesis of $C_{60}$ Molecule Triggers Intense Research Effort", *C & EN*, 22–25.

Chang (1953) "Effect of Temperature on Movement of a Chromatographic Zone", *Analytical Chemistry* 25, 1235–1237.

Cox, et al. (1991) "Characterization of $C_{60}$ and $C_{70}$ Clusters", *J. Am. Chem. Soc.* 113, 2940–2944.

Cram (1986) "Preorganization—From Solvents to Spherands", *Angw. Chem. Int. Ed. Engl.* 25, 1039–1057.

Dayan, et al. (1991) "Regulation of Molecular Conformation of Chiral Tripodal Structures by $Ca^{2+}$ Binding", *American Chemical Society* 113, 3431–3439.

Dunn, et al. (1990) "Versatile Methods for the Synthesis of Differentially Functionalized Pentaerythritol Amine Derivatives", *J. Org. Chem.* 55, 6368–6373.

Fleischer, et al. (1971) "Conversion of Aliphatic and Alicyclic Polyalcohols to the Corresponding Primary Polyamines", *J. Org. Chem.* 36, 3042–3044.

Guggi, et al. (1976) "Neutraler Ionophor fur Flussigmembranelektroden mit honer Selektivitat fur Natrium—Gegenuber Kalium–Ionen", *Helvetica Chimica Acta* 59, 2417–2420.

Hawkins, et al. (1990) "Organic Chemistry of $C_{60}$ (Buckminsterfullerene): Chromatography and Osmylation", *J. Org. Chem.* 55, 6250–6252.

Howard, et al. (1991) "Fullerenes $C_{60}$ and $C_{70}$ in Flames", *Nature* 352, 139–141.

Jinno, et al. (1992) "Liquid Chromatographic Separation of All–Carbon Molecules $C_{60}$ and $C_{70}$ with Multi–Legged Phenyl Group Bonded Silica Phases", *Journal of Chromatography* 594, 105–109.

Johnson, et al. (1990) "$C_{60}$ has Icosahedral Symmetry", *J. Am. Chem. Soc.* 112, 8984–8985.

Kikuchi, et al. (1991) "Separation, Detection and UV/Visible Absorption Spectra of Fullerenes; $C_{76}$, $C_{78}$ and $C_{84}$", *Chem. Letters,* No. 9, 1607–1610.

Kratschmer, et al. (1990) "Solid $C_{60}$: A New Form of Carbon", *Nature* 347, 354–358.

Kroto, et al. (1991) "$C_{60}$: Buckminsterfullerene", *Chem. Rev.* 91, 1213–1235.

Krusic, et al. (1991) "Radical Reactions of $C_{60}$", *Science* 254, 1183–1185.

Lochmuller (1980) "Chemically–Bonded, Charge Transfer Acceptors for High–Performance Liquid Chromatography", *Midland Macromolecular Symposium on Silylated Surfaces for High Performance Liquid Chromatography,* 231.

Maggs (1969) "The Role of Temperatures in Liquid–Solid Chromatography: Some Practical Consideration", *Journal of Chromatographic Science* 7, 145–151.

Nondek (1986) "Liquid Chromatography on Chemically Bonded Electron Donors and Acceptors", *Journal of Chromatography* 373, 61–80.

Pirkle, et al. (1991) "A Convenient Void Volume Marker for Several Chiral HPLC Columns", *Journal of Liquid Chromatogrpahy* 14, 1–8.

Pirkle, et al. (1991) "An Unusual Effect of Temperature on the Chromatographic Behavior of Buckminsterfullerene", *J. Org. Chem.* 56, 6973–6974.

Roush, et al. (1985) "Cascade Molecules: A New Approach to Micelles: A [27]–Arborol", *J. Org. Chem.* 50, 2003–2004.

Suzuki, et al. (1991) "Systematic Inflation of Buckminsterfullerence $C_{60}$: Synthesis of Diphenyl Fulleroids $C_{61}$ to $C_{66}$", *Science* 254, 1186–1188.

Taylor, et al. (1990) "Isolation, Separation and Characterization of the Fullerenes $C_{60}$ and $C_{70}$: The Third Form of Carbon", *J. Chem. Soc. Commun.,* 1423–1425.

Tor, et al. (1987) "A Trispeptide Circularly Organized Through Inter–Chain Hydrogen Bonds", *J. Chem. Soc. Commun.,* 749–750.

Tor, et al. (1987) "Biometic Ferric Ion Carriers. A Chiral Analogue of Enterobactin", *J. Am. Chem. Soc.* 109, 6517–6518.

Weibull, et al. (1962) "The Synthesis of Some 1,1, 1–Trishydroxymethylalkanes", *Acta Chem. Scand.* 16, 1062.

Welch, et al. (1992) "Progress in the Design of Selectors for Buckminsterfullerenes", *Journ. of Chem.* 609, 89–101.

PREPARATIVE SEPARATION OF $C_{60}$ AND $C_{70}$ CARRIED OUT AT ROOM TEMPERATURE (ABOUT 23°C)

PREPARATIVE SEPARATION OF $C_{60}$ AND $C_{70}$ CARRIED OUT AT 90°C

RECOGNITION AND SEPARATION OF CARBON CLUSTERS

The invention described herein was made with Government support under Grant NSF CHE 87-14950 awarded by The National Science Foundation. The Government has certain rights in the invention. This is a continuation of application Ser. No. 874,791, filed on Apr. 27, 1992, now U.S. Pat. No. 5,338,529.

BACKGROUND OF THE INVENTION

1. Field of the Invention

The present invention relates to the recognition and separation of carbon clusters. In one aspect, the invention is directed to a recognition selector useful, for example, as a stationary phase in the chromatographic separation of carbon clusters, such as $C_{60}$ and $C_{70}$ fullerenes. In another aspect, the invention is directed to the use of elevated temperatures to obtain improved separation of carbon clusters, such as $C_{60}$ and $C_{70}$ fullerenes.

2. Description of the Prior Art

Solid, or elemental, carbon has for some time been thought to exist in only two forms: diamond, wherein the structure is face-centered cubic with each carbon atom bonded to four other carbon atoms in the form of a tetrahedron: and graphite, which has layers of carbon atoms arranged in the form of hexagons lying in planes, the carbon atoms of various layers being aligned with each other.

Recently, a third form of solid carbon has been discovered. Unlike diamond and graphite, however, this new form of carbon has the structure of a closed shell. This family of closed carbon shells, also referred to herein as carbon clusters, include for example that group of closed carbon shells denominated in the art as the fullerenes, such as those highly stable molecules known as Buckminsterfullerene, and the related molecule known as fullerene-70; other members of the fullerene family include, e.g., $C_{78}$ and $C_{240}$.

Buckminsterfullerene, also known as $C_{60}$, is a 60 carbon atom molecule having the geometry of a truncated icosahedron; that is, a polygon with 60 vertices whereat the carbon atoms are placed, and 32 faces, 12 of which are pentagons and 20 of which are hexagons. $C_{60}$ thus has the geometry of a soccerball.

Fullerene-70, also known as $C_{70}$, is similar to $C_{60}$, only it has 10 additional carbon atoms which are believed to be inserted as a band of hexagons around the middle of the truncated icosahedron.

Although only recently discovered, various routes for synthesizing fullerenes are already available. An aspect of fullerene production that is of especial importance is the separation of fullerenes, as a whole, from a resultant fullerene-containing product admixture, as well as the separation of the various species of fullerenes from each other.

Presently known separation techniques include the method described by Taylor, et al. in *J. Chem. Soc., Chem. Commun.*, pp. 1423–1425 (1990). This method employs solvent extraction to remove $C_{60}$ and $C_{70}$ from carbon product deposits, followed by chromatographic separation using alumina and hexane to separate $C_{60}$ from $C_{70}$.

Another approach, which is reported by Hawkins, et al. in *J. Org. Chem.*, 55, pp. 6250–6252 (1990) entails the use of flash chromatography by dry loading onto silica gel, and elution with hexanes to achieve a 40% recovery of material that is almost exclusively $C_{60}$ and $C_{70}$. $C_{60}$ and $C_{70}$ are then separated chromatographically using a commercially available N-3,5-(dinitrobenzoyl)-phenylglycine derived stationary phase eluted with hexane. Cox, et al. have also described the chromatographic purification of $C_{60}$ and $C_{70}$ using a K-acidic dinitroaniline stationary phase in *J. Amer. Chem. Soc.*, 113, pp. 2940 (1991).

Notwithstanding these developments, the methods for separating and purifying fullerenes, as known heretofore, have been only marginally successful insofar as practical analytic and, more importantly, preparative scale applications are concerned. For example, the chromatographic separations that are described by Taylor, et al. and Hawkins, et al. are impractical for preparative scale preparation of fullerenes because of the extreme insolubility of the fullerene analytes in the mobile phase. This condition limits, for example, the sample sizes which can be separated per run.

Thus there continues to be a pressing need for a method of separating fullerenes in a manner that is qualitatively and quantitatively superior to known methods, and that will be of practical utility in both the analytic and preparative scale separation of carbon clusters, such as $C_{60}$ and $C_{70}$ fullerenes.

SUMMARY OF THE INVENTION

The present invention overcomes the inadequacies attendant carbon cluster separation methods known hitherto. In one aspect, the present invention is directed to a recognition selector having the formula described hereinbelow, which formula provides multiple K-acidic sites arranged in a concave-like shape that is complementary to the convex-like surface shape of a carbon cluster molecule. The recognition selector of the invention is thus capable of undergoing simultaneous multipoint interactions with carbon cluster molecules, particularly $C_{60}$ and $C_{70}$ fullerenes.

The recognition selector of the invention is a compound having the formula:

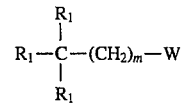

wherein $R_1$ is

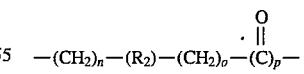

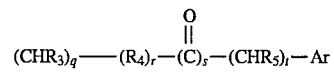

and wherein $R_2$ is O, S or $NR_{12}$ wherein $R_{12}$ is independently hydrogen or P=O with the proviso that when $R_{12}$ is P=O, then only one such group is present and all $R_2$'s are additionally bonded to $R_{12}$; $R_4$ is independently O, S or NH; $R_3$ and $R_5$ are each independently hydrogen or lower alkyl; n and o are each independently zero, 1, 2 or 3; p, q, r, s and t are each independently zero or 1 and Ar is a monocyclic or ortho-fused polycyclic aromatic moiety having up to 10 carbon atoms, either of which may be unsubstituted or substituted with one or more lower alkyl, $NO_2$, $N(R_6)_3^+$, CN

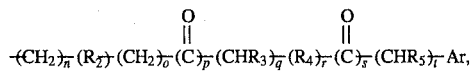

COOR$_7$ SO$_3$H COR$_8$ and OR$_9$ wherein R$_6$, R$_7$, R$_8$ and R$_9$ are each independently hydrogen or lower alkyl; W is H or CH=CH$_2$; and m is 1 to 10.

In an embodiment of the present invention, the above-described recognition selector is employed in a method for separating a carbon cluster, such as a fullerene, from a mixture containing at least one carbon cluster which comprises contacting a mixture containing at least one carbon cluster with the recognition selector described above, under conditions effective to form a complex between said carbon cluster and said recognition selector, separating said complex from said mixture and recovering said carbon cluster from said complex.

In another embodiment, the present invention is also directed to an apparatus, such as a liquid membrane separation system or a liquid chromatographic column, such as a high performance liquid chromatographic (HPLC) column, that employs the recognition selector described above.

In still another embodiment, the present invention is directed to the use of elevated temperatures to obtain improved chromatographic separation of carbon clusters.

DETAILED DESCRIPTION OF THE INVENTION

Figure 1:
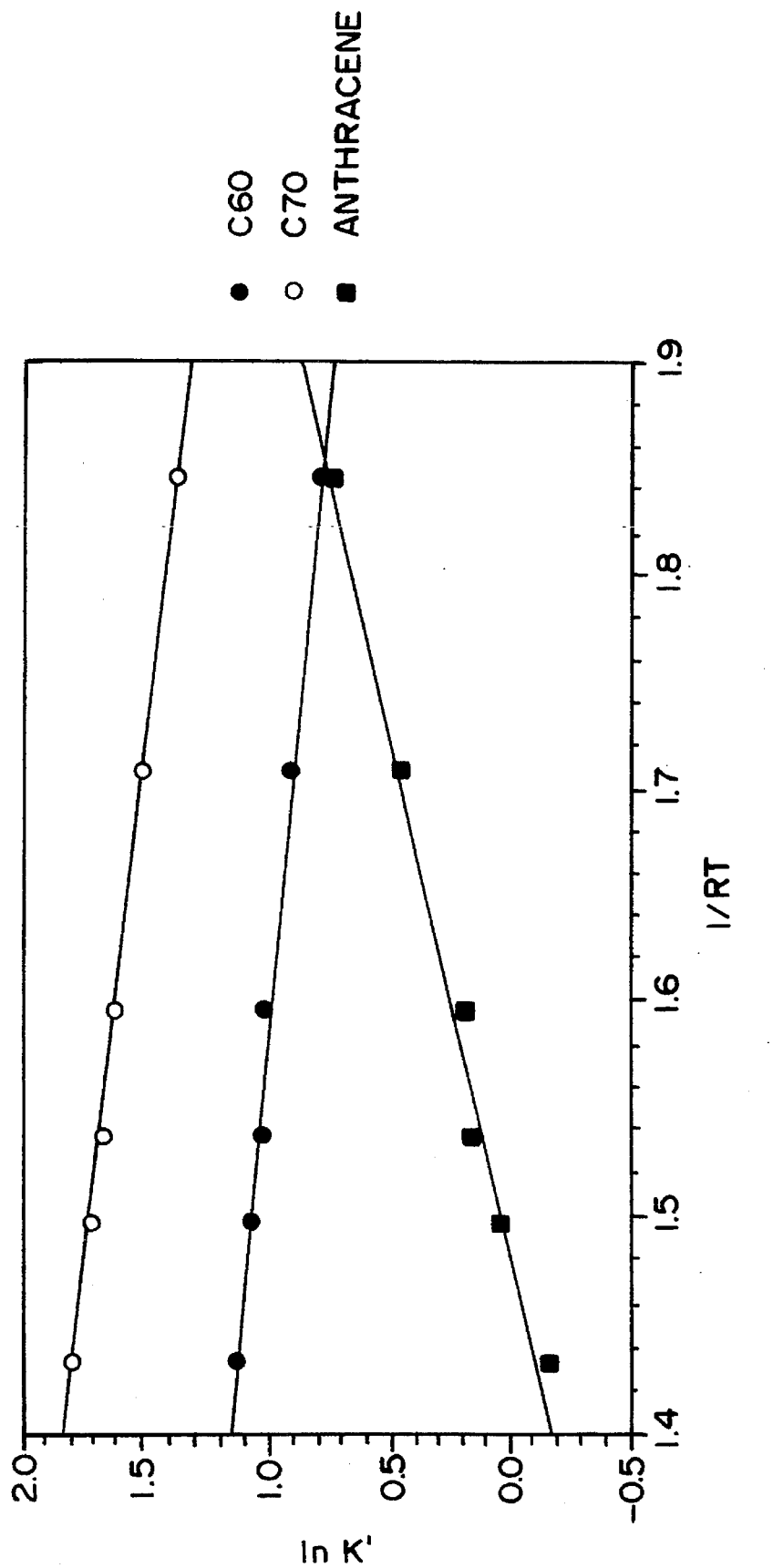
FIG. 1 is a graph depicting the affect of temperature on the retention of $C_{60}$, $C_{70}$ and anthracene.

The present invention is directed to a method for recognizing and separating carbon clusters, particularly those compounds known as fullerenes and more particularly those known as $C_{60}$ to $C_{70}$. The method employs a recognition selector compound having the formula described below. Significantly, in the practice of the invention, a qualitative and quantitative increase in the separation of fullerenes is obtained as compared to methods previously known.

The recognition selector of the present invention is a compound having the following formula:

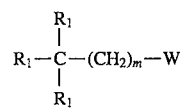

wherein R$_1$ is wherein

R$_2$ is O, S or NR$_{12}$ wherein R$_{12}$ is independently hydrogen or P=O with the proviso that when R$_{12}$ is P=O, then only one such group is present and all R$_2$'s are additionally bonded to R$_{12}$;

R$_4$ is independently O, S or NH,

R$_3$ and R$_5$ are each independently hydrogen or lower alkyl, n and o are each independently zero, 1, 2 or 3, p, q, r, s and t are each independently zero or 1, Ar is a monocyclic or ortho-fused polycyclic aromatic moiety having up to 10 carbon atoms, either of which may be unsubstituted or substituted with one or more lower alkyl, $NO_2$, $N(R_6)^+_3$, CN, COOR$_7$, SO$_3$H, COR$_8$ and OR$_9$ groups wherein R$_6$, R$_7$, R$_8$ and R$_9$ are each independently hydrogen or lower alkyl;

W is H or CH=CH$_2$; and m is 1 to 10.

As employed herein, the lower alkyl groups contain up to 6 carbon atoms which may be in the normal or branched configuration, including methyl, ethyl, propyl, isopropyl, butyl, isobutyl, t-butyl, amyl, pentyl, hexyl and the like. The preferred alkyl group contains 1 to 3 carbon atoms; methyl is particularly preferred.

The monocyclic or ortho-fused polycyclic aromatic moiety having up to 10 carbon atoms includes, e.g., phenyl, α-naphthyl and β-naphthyl. Preferred substituted monocyclic aromatic moieties include 3,5-dinitrophenyl and 2,4-dinitrophenyl. Preferred substituted polycyclic aromatic moieties include 6-methoxy-β-naphthyl and 7-methoxy-β-naphthyl.

In a first preferred embodiment of the recognition selector of the present invention, n and p are each 1; o, q, r, s and t are each zero; R$_2$ is O; Ar is 3,5-dinitrophenyl; m is 7; and W is CH=CH$_2$. The recognition selector of this first preferred embodiment is denoted hereinafter as RS 3. The structure of RS 3 is shown below.

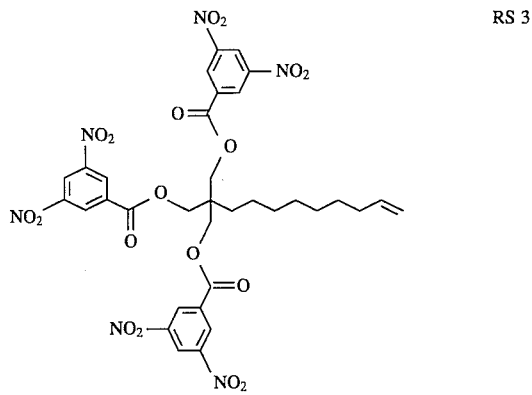

In a second preferred embodiment of the recognition selector of the present invention, n and p are each 1; o, q, r, s and t are each zero; R$_2$ is NH; Ar is 3,5-dinitrophenyl; m is 7; and W is CH=CH$_2$. The recognition selector of this second preferred embodiment is denoted hereinafter as RS 5. The structure of RS 5 is shown below.

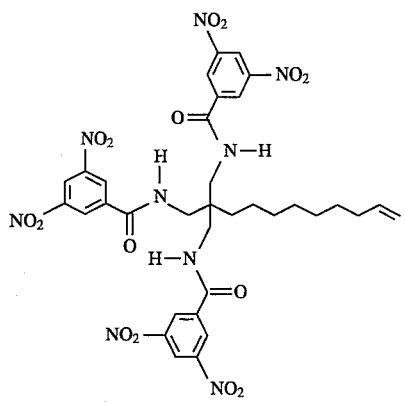

In a third preferred embodiment of the recognition selector of the present invention, n, o, p and r are each 1; q, s and t are each zero; $R_2$ is O; $R_4$ is NH; Ar is 3,5-dinitrophenyl; m is 7; and W is CH=CH$_2$. The recognition selector of this third embodiment is denoted hereinafter as RS 6. The structure of RS 6 is shown below.

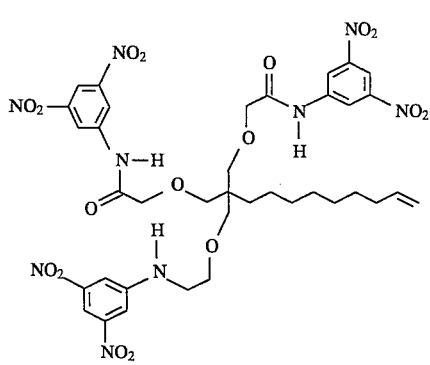

In a fourth preferred embodiment of the recognition selector of the present invention, n is 1; o, p, q, r, s and t are each zero; $R_2$ is O, Ar is 2,4-dinitrophenyl; m is 7; and W is CH=CH$_2$. The recognition selector of this fourth embodiment is denoted hereinafter as RS7. The structure of RS 7 is shown below.

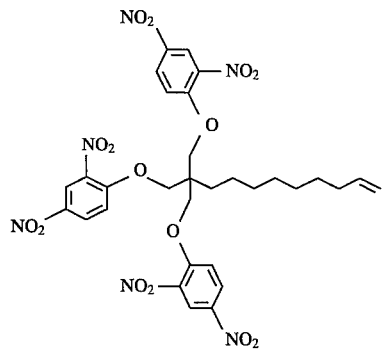

In a fifth preferred embodiment of the recognition selector of the present invention, n, p, q, r and s are each 1; o and t are each zero; $R_2$ and $R_4$ are each NH; $R_3$ is isobutyl; Ar is 3,5-dinitrophenyl; m is 7 and W is CH=CH$_2$. The recognition selector of this fifth embodiment is denoted hereinafter as RS 8.

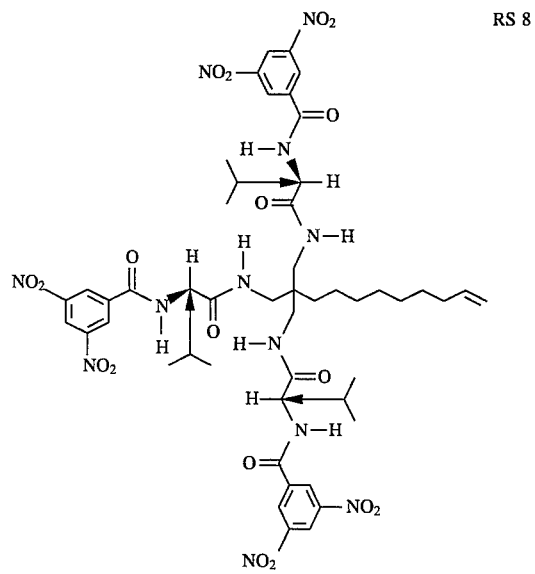

In a sixth preferred embodiment of the recognition selector of the present invention, n, p, q and r are each 1; o, s and t are each zero; $R_2$ is O; $R_3$ is CH$_3$; $R_4$ is NH, Ar is β-naphthyl; m is 6; and W is CH=CH$_2$. The recognition selector of this sixth embodiment is denoted hereinafter as RS9. The structure of RS 9 is shown below.

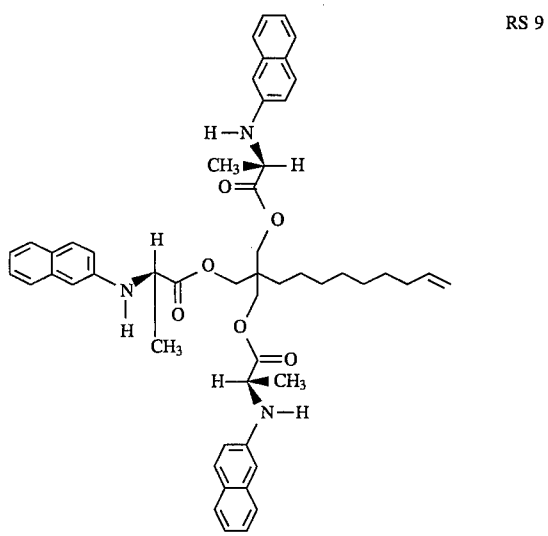

In a seventh preferred embodiment of the recognition selector of the present invention, n, p and q are each o, r, s and t are each zero; $R_2$ is O; $R_3$ is CH$_3$; Ar is 6-methoxy-β-naphthyl; m is 7 and W is CH=CH$_2$. The recognition selector of this seventh embodiment is denoted hereinafter as RS10. The structure of RS10 is shown below.

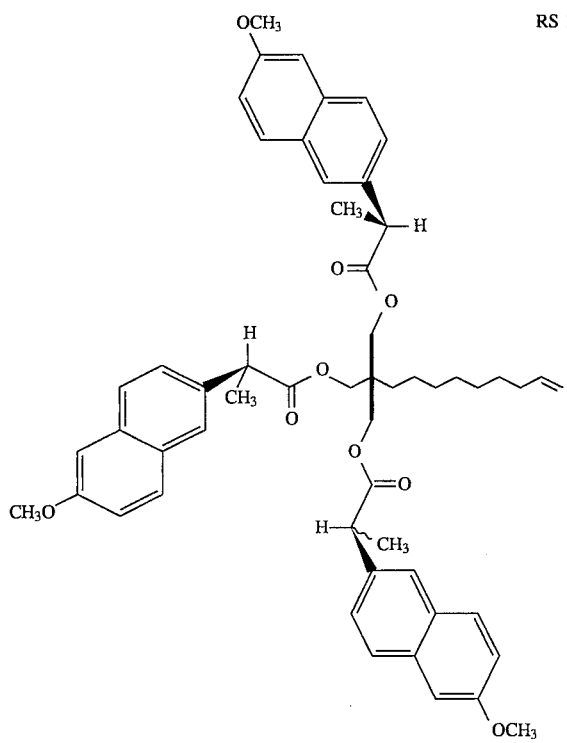

In an eighth preferred embodiment of the recognition selector of the present invention, n, o, p, r and t are each 1; q and s are each zero; $R_2$ is O; $R_4$ is NH; $R_5$ is $CH_3$; Ar is α-naphthyl; m is 7; and W is $CH=CH_2$. The recognition selector of this eighth embodiment is denoted hereinafter as RS11. The structure of RS 11 is shown below.

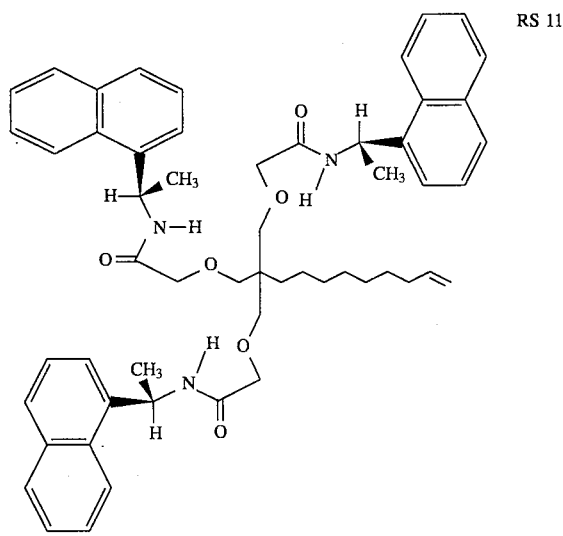

In a ninth preferred embodiment of the recognition selector of the present invention, n and q are each 1; o, p, r, s and t are each zero; $R_2$ is $NR_{12}$ and $R_{12}$ is P=O with the proviso that only one such P=O group is present and all $R_2$'s are additionally bonded to said P=O group; Ar is α-naphthyl; m is 7 and W is $CH=CH_2$. The recognition selector of this ninth embodiment is denoted hereinafter as RS12. The structure of RS12 is shown below.

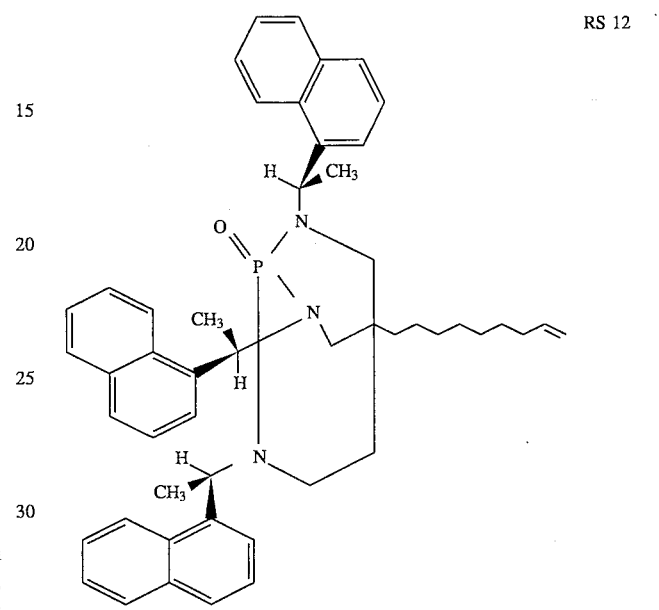

The recognition selectors of the present invention may be prepared by conventional chemical preparative techniques. The recognition selectors of the present invention may be utilized to form a stationary phase of an HPLC column by techniques known in the art. A preferred technique in this regard includes hydrosilation followed by immobilization on a support effective for use in chromatographic separation, such as silica (denoted herein as $SiO_2$) or alumina. For illustrative purposes the preparation of recognition selectors RS 3 and RS 7 are described below, but one skilled in the art will readily appreciate the modifications necessary to prepare other recognition selectors within the scope of the chemical formula that is described herein.

The synthetic sequence used to prepare RS 3 is shown below in Table 1.

TABLE 1

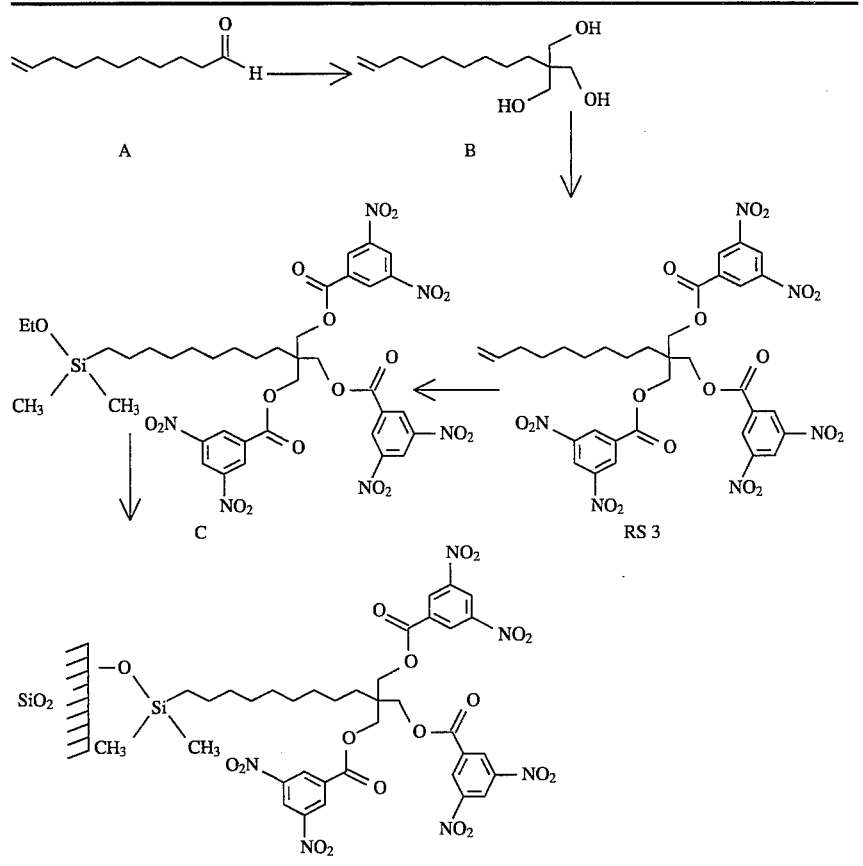

This preparation begins with an aldehyde, ω-undecenylenyl aldehyde (A). This aldehyde has a terminal double bond which serves as a means for attachment to silica to form a stationary phase in an HPLC column. Treatment of the aldehyde with formaldehyde under basic conditions using potassium hydroxide, ethanol and water, provides the triol (B). The triol is acylated with 3,5-dinitrobenzoyl chloride in triethylamine and dichloromethane to afford the triester, RS 3. Hydrosilation using dimethylchlorosilane, chloroplatinic acid (cat) and dichloromethane, followed by treatment with ethanol, triethylamine and ethyl ether affords the silane (C). Immobilization on silica gel (5 μ/100 Å silica gel, 120° C., 1 torr, 24 hr) affords stationary phase RSP 3.

The synthetic sequence used to prepare RS 7 is shown below in Table 2.

TABLE 2

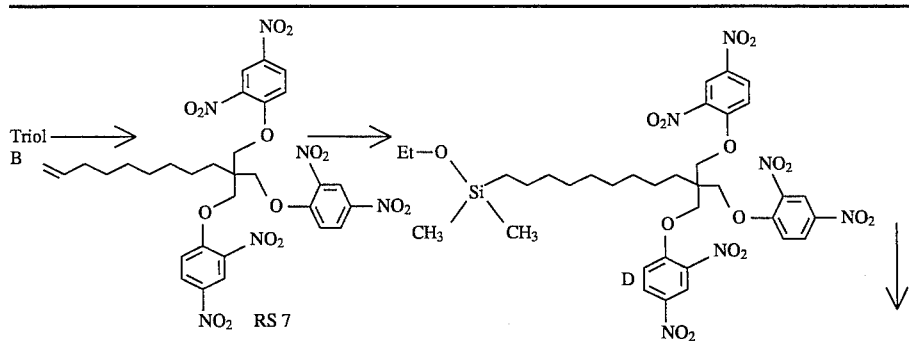

TABLE 2-continued

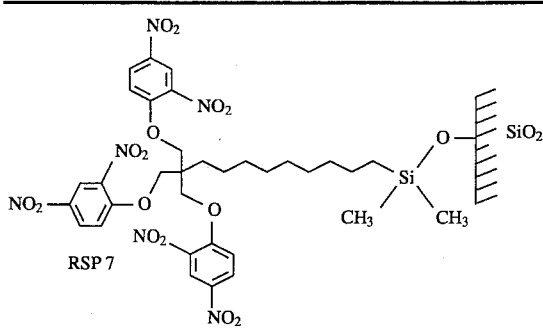

RSP 7

The triol (B) prepared as described above, is reacted with 2,4-dinitrofluorobenzene in triethylamine and dichloromethane to yield the triether, RS 7. Hydrosilation of triether RS 7 with dimethylchlorsilane, chloroplatinic acid (cat) and dichloromethane, followed by treatment with ethanol, triethylamine and ethyl ether affords the silane, D. Bonding of the silane to silica gel (5µ/100 Å silica gel, 120° C., 1 torr, 24 hr) affords stationary phase RSP 7.

Separation of carbon clusters such as fullerenes using the recognition selector of the invention may be achieved in a variety of techniques known in the art. In one embodiment, the recognition selector may form the active portion of the stationary phase in an HPLC column as described above. In this embodiment of the present invention, the terminal W of the formula is preferably $CH=CH_2$ so as to permit the chiral selector to be immobilized on a support which is suitable for use in chromatographic separations. Supports in this regard include, e.g., silica and alumina. In one configuration, the recognition selector is immobilized by covalently bonding it to silica. Those recognition selectors of the instant invention that are optically active, may, if desired, be separated into the R or S enantiomer for use as the active portion of the stationary phase in the column and may thus also be employed in enantiomeric separations.

The effect of temperature on the chromatographic behavior of fullerenes is unusual. Generally, in chromatographic separations, the thermodynamic parameters of adsorption indicate that a loss of entropy accompanies exothermic adsorption. Thus, as a rule, an increase in chromatographic column temperature translates into a lessening of analyte retention. It is in this regard that the behavior of fullerenes is unusual; that is, the retention of fullerenes such as $C_{60}$ and $C_{70}$ increases rather than decreases when column temperature is increased. This unusual temperature dependence of fullerene retention has been observed to occur in a variety of mobile phases and with several different π-acidic and π-basic stationary phases. Since polynuclear aromatic dopants, such as anthracene and naphthalene, exhibit normal retention behavior under the same conditions, the unusual temperature effect relative to fullerenes seems to be analyte dependent and not column or mobile phase dependent.

Fullerenes, such as $C_{60}$ and $C_{70}$, are, in the normal course of chromatographic separation, present in solution with, e.g., benzene. Thus an increase in column temperature leads to markedly improved bandshapes and resolution of $C_{60}$ and $C_{70}$: the higher column temperature leads to an increase in the retention of the fullerenes while simultaneously causing a decrease in retention time of the solvent. Improved separation of fullerenes using this unusual temperature effect can be obtained on chromatographic columns utilizing a stationary phase formed from the recognition selector of the invention, as well as on commercially available columns. Examples of commercially available columns include those whose stationary phases incorporate as an active part, 3,5-dinitrobenzoyl leucine, 3,5-dinitrobenzoyl phenylglycine, naphthylalanine and naphthyl leucine. These columns are commercially available from Regis Chemical Company, Morton Grove, Illinois.

An example of the effect of temperature on the retention of $C_{60}$ and $C_{70}$ is shown in FIG. 1. As shown in FIG. 1, a commercially available column obtained from Regis Chemical Company employing a stationary phase of (R)-N-(3,5-dinitrobenzoyl)phenylglycine (4.6 mm I.D.×25 cm length) was used to study the effect of temperature on $C_{60}$, $C_{70}$ and anthracene. All samples were dissolved in a mobile phase of 10% dichloromethane in hexane prior to injection. Flow rate was 2.00 ml/min. and void time was determined by injection of 1,3,5-tri-t-butylbenzene, as described by Pirkle, et al. in J. Liq. Chrom., 14, 1, 1991 the contents of which are incorporated herein by reference. As seen by FIG. 1, as column temperature increased, the retention of $C_{60}$ and $C_{70}$ increased; whereas the retention of anthracene decreased.

Figure 2A:
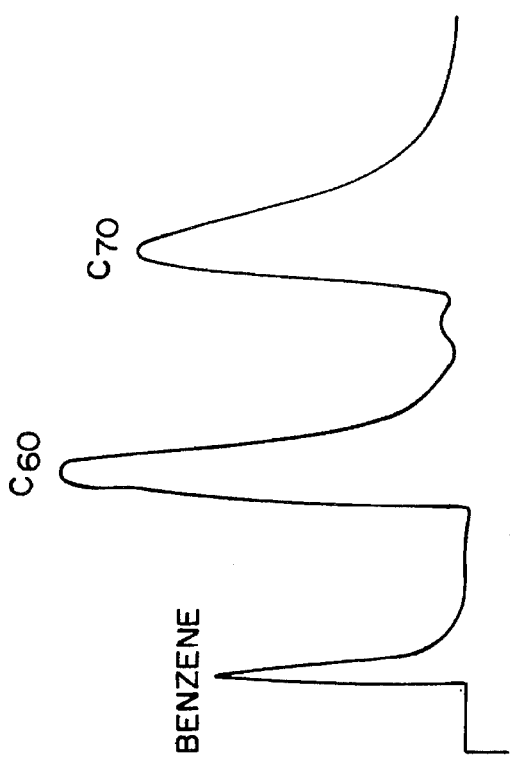
FIG. 2A is a graph showing the preparative separation of $C_{60}$ and $C_{70}$ at room temperature.
Figure 2B:
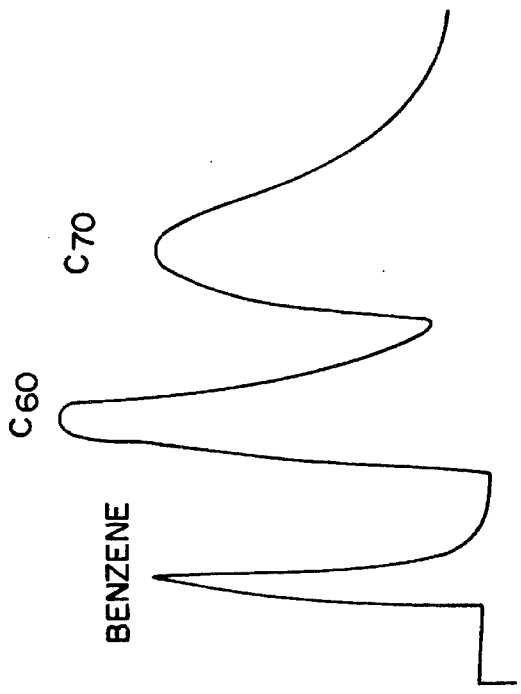
FIG. 2B is a graph showing the preparative separation of $C_{60}$ and $C_{70}$ at 90° C.

The practical effect of this unusual temperature dependence is shown in FIGS. 2A and 2B. The column utilized to generate the preparative separations shown in FIGS. 2A and 2B was obtained from Regis Chemical Company and employed a (R)-3,5-(dinitrobenzoyl)phenylglycine (21.1 mm I.D.×25 cm length) as a stationary phase. Flow rate was 9 ml/min.; mobile phase was hexane. The sample utilized in each case was a 500 µl injection of a 6 mg/ml benzene solution of $C_{60}$ and $C_{70}$. A comparison of FIG. 2A, wherein separation was carried out at room temperature (about 23° C.), and FIG. 2B, wherein separation was carried out at 90° C., shows an improvement in bandshape and resolution when the higher temperature is used.

The increased column temperatures contemplated by the present invention are temperatures that are higher than room temperature, preferably in the range from over about room temperature (about 25° C.) to about 120° C. More preferably, the increased temperature range is between about 80° C. to about 100° C. Most preferably, column temperature is about 90° C.

In another embodiment, the recognition selector of the invention may be utilized to effect separations employing semi-permeable membranes wherein the recognition selector forms part of a mobile phase. Such techniques include the use of semi-permeable membranes that are in the form of hollow fiber membranes. In this embodiment of the invention, it is preferred that the terminal W in the formula of the recognition selector be hydrogen so as to minimize covalent bonding by the recognition selector. In one particularly useful embodiment, the recognition selector forms part of a liquid membrane passing on one side of a semi-permeable barrier with the fullerenes to be separated passing on the other side of the barrier. The pores of the barrier become impregnated with the liquid membrane containing the recognition selector. A fullerene or species of fullerene complexes with the recognition selector, passes through the barrier into the moving liquid membrane and is conducted to a second location where dissociation of the complex takes place thus allowing the fullerene to be recovered. This technique is generally disclosed in commonly assigned U.S. patent application Ser. No. 528,007, filed May 23, 1990, now U.S. Pat. No. 5,080,795 the contents of which are incorporated herein by reference.

The following examples are given to illustrate the scope of the invention. Because these examples are given for illustrative purposes only, the invention embodied therein should not be limited thereto.

EXAMPLES

A series of experiments was conducted to examine the chromatographic behavior of $C_{60}$ and $C_{70}$ and eight polycyclic aromatic hydrocarbons using stationary phases formed from the recognition selector of the present invention, and to compare this behavior with commercially available stationary phases, as well as four different π-acidic stationary phases that were especially prepared for purposes of these experiments.

The polycyclic aromatic hydrocarbons and the fullerenes that were used in these studies are shown in Table 3, below.

TABLE 3

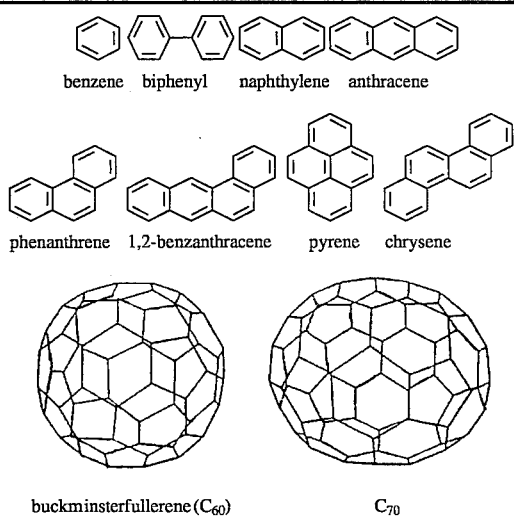

HPLC columns having four different commercially available stationary phases were obtained from Regis Chemical Company, Morton Grove, Ill. These stationary phases, denominated for experimental purposes as SP 1, SP 2, SP 3 and SP 4, are depicted in Table 4, below.

TABLE 4

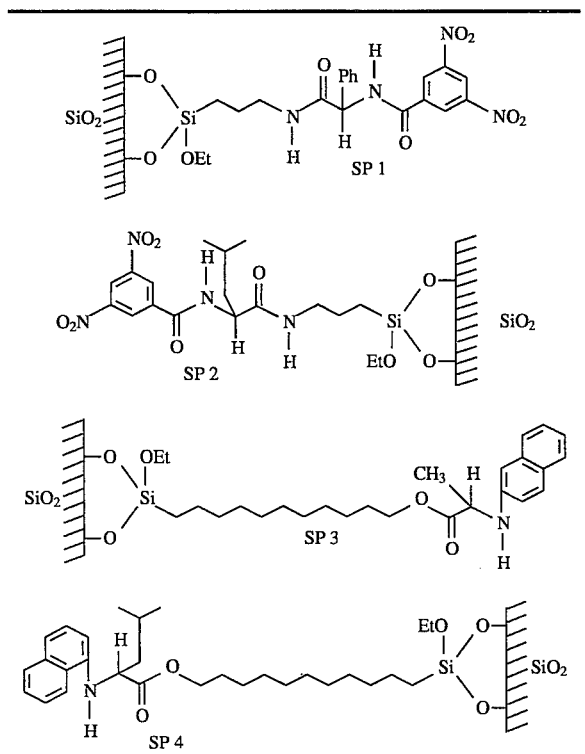

APPARATUS

Chromatographic analysis was performed using a Beckman-Altex 100-A pump, a Rheodyne Model 7125 injector with a 20 μl sample loop, a linear UVIS 200 variable wavelength absorbance monitor set at 254 nm, and the Hewlett-Packard HP 3394-A integrating recorder.

MATERIALS

Rexchrom™ 5μ/100 Å silica gel and columns containing stationary phases SP 1–4 were obtained from Regis Chemical Company, Morton Grove, IL. Dimethylchlorosilane and 4-aminobutyldimethylmethoxysilane were obtained from Petrarch Systems, Bristol, Pa.

METHODS

All chromatographic experiments were carried out at a nominal flow rate of 2.00 ml/min. Column void time was determined by injection of tri-t-butylbenzene in the manner reported by Pirkle, et al. in *J. Liq. Chrom.*, 14, pp. 1–8, 1991 the contents of which are incorporated herein by reference.

SYNTHESIS

The four K-acidic stationary phases, SP 5, SP 6, SP 7 and SP 8, that were prepared for comparative purposes and immobilized on silica are shown in Table 5, below.

TABLE 5

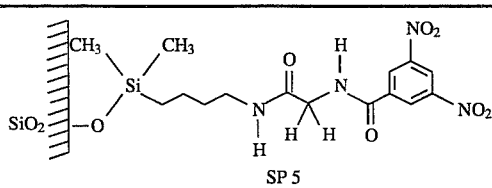

TABLE 5-continued

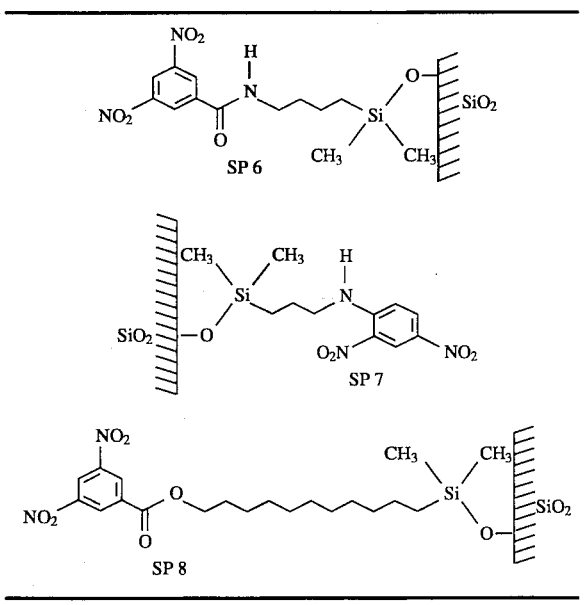

PREPARATION OF SP 5
The synthetic route for SP 5, which was an achiral glycine analog is shown below:

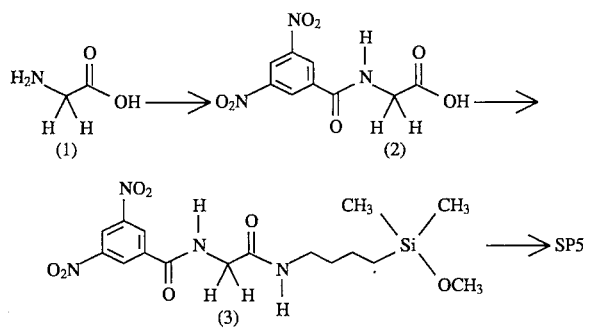

Preparation of 3,5-(Dinitrobenzamido)glycine, (2): Glycine ((1), 5.0 g) was suspended in 100 ml dry tetrahydrofuran (THF) and cooled in an ice bath. 3,5-dinitrobenzoyl chloride (16.9 g) and propylene oxide (7.0 ml) were added, and the mixture was stirred under a nitrogen atmosphere while gradually warming to room temperature. After 10 h the crude reaction mixture was evaporated to afford a brown oil. Addition of 100 ml of dichloromethane resulted in crystallization after several minutes. Filtration followed by several washes with dichloromethane and drying under high vacuum gave 13.9 g of 3,5-(Dinitrobenzamido)glycine, (2), (78% yield) as a pale yellow powder. $^1$H NMR (d$_6$ DMSO)δ: 12.8 (s,1H), 9.6(t,1H), 9.1 (s,2H), 9.0 (s,1H), 4.0 (d,2H).

Preparation of the Organosilane (3): To a cooled (ice bath) solution of 1.0 g of 3,5-(Dinitrobenzamido)glycine, (2), in tetrahydrofuran was added 0.92 g of 1-ethoxy-carbonyl-2-ethoxyl-1,2-dihydroguinoline (EEDQ). After stirring 45 minutes under a nitrogen atmosphere, 0.50 g of 4-aminobutyldimethylmethoxysilane was added and the reaction mixture was allowed to gradually warm to room temperature. After 10 h the crude reaction mixture was evaporated and purified by flash chromatography on silica to give 0.65 g (42% yield) of silanized 3,5-(Dinitrobenzamido)glycine, (3), as a slightly pink foam.

Silica gel (5.0 g, Rexchrom™, 5 µ/100 Å) was placed in a round bottom flask fitted with a Dean-Stark trap, condenser, and boiling stick. About 30 ml of benzene were added, and the mixture was refluxed for several hours. Dimethylformamide (1 mL) was then added to the benzene slurry, and the sample was evaporated to near dryness on a rotary evaporator. A dichloromethane solution of silanized 3,5-(Dinitrobenzamido)glycine, (3), (0.65 g) was then added, and the resulting slurry was sonicated for several minutes before being evaporated to near dryness. The sample was again slurried in dichloromethane, sonicated, and evaporated to near dryness, this sequence being repeated several times to insure complete coverage of the silica gel. The nearly dry silica gel-silane compound (3) mixture was then heated on an oil bath under reduced pressure (130° C., 1 mm Hg, 18 hours). The silica gel was then slurried in ethanol, filtered through a fine sintered glass funnel, and washed repeatedly with ethanol, and then methanol. Evaporation and analysis of the ethanol washes could have been performed at this point to look for degradation of the silane compound (3) during the course of the bonding reaction. The washed silica gel was then slurried in methanol and packed into a 4.6 mm I.D.×25 cm length stainless steel HPLC column using an air driven Haskell pump operating at about 9000 psi. Recovered excess stationary phase from the column packer was dried thoroughly under high vacuum and submitted for elemental analysis (C 3.39%) which indicated a loading of $1.9 \times 10^{-4}$ moles of selector per gram of stationary phase. Residual silanols on the chromatographic support were then a "endcapped" by passing a solution of 1 ml hexamethyldisilazane dissolved in 50 ml dichloromethane through the dichloromethane-equilibrated column at a flow rate of 1 ml/min. The column was then sequentially eluted with dichloromethane, methanol, and 20% 2-propanol in hexane.

PREPARATION OF SP 6
The synthetic route for SP 6, which contained an isolated 3,5-dinitrobenzamide system, is shown below.

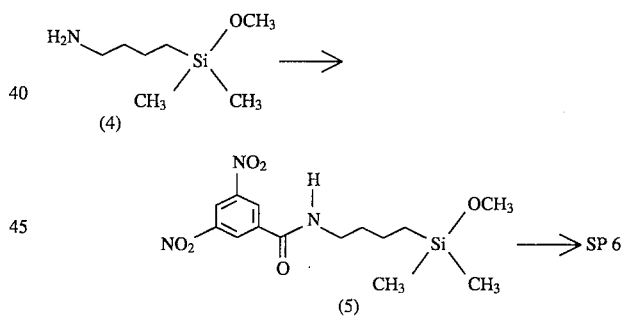

Preparation of the Organosilane, (5): Triethylamine (0.69 g) and 4-aminobutyldimethylmethoxysilane, (4), (1.00 g) were dissolved in 20 mL dichloromethane and cooled in an ice bath. 3,5-dinitrobenzoyl chloride (1.43 g) dissolved in 10 ml of dichloromethane, was then added dropwise over several minutes with stirring under a nitrogen atmosphere. The reaction mixture was allowed to warm to room temperature and stirred for an additional hour. The crude reaction mixture was evaporated to dryness and purified by flash chromatography (silica gel, 5% acetonitrile/dichloromethane) to afford the organosilane (5) as a clear oil (840 mg, 69.4% yield). $^1$H NMR (CDCl$_3$)δ: 9.15 (s,1H), 9.0 (s,1H), 6.8 (bs,1H), 3.55 (m,2H), 4.3 (s,3H), 1.75 (m,2H), 1.5 (m,2H), 0.65 (t,2H), 0.15 (s,6H).

Bonding of the organosilane (5) to silica, and packing of the resulting stationary phase into an HPLC column followed the procedure reported for the preparation of stationary phase SP 5, except that a Kügelrohr distillation apparatus was used in the bonding reaction (130° C., 1 mm Hg, 18 hours). Stationary phase recovered from the column packer was submitted for elemental analysis (C 4.69%) which indicated a loading of 3.0×10$^{-4}$ moles of selector per gram of stationary phase.

PREPARATION OF SP 7

The synthetic route for SP 7, which contained a 2,4-dinitroaniline system, is shown below:

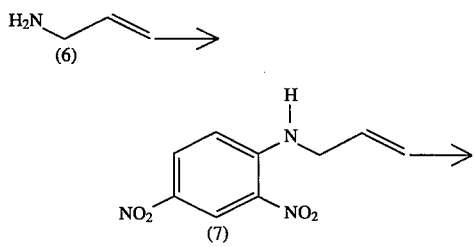

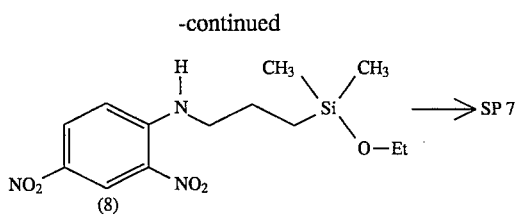

Preparation of the Olefin, (7): To a cooled, stirred solution of allylamine ((6), 0.46 g) and triethylamine (0.90 g) in dichloromethane, was added 2,4-dinitrofluorobenzene (1.5 g). After warming to room temperature, the reaction mixture was stirred for three hours, then evaporated to dryness and purified by flash chromatography (silica, dichloromethane) to afford olefin (7) as a crystalline solid (1.09 g, 61% yield). $^1$H NMR (CDCl$_3$)δ:9.25 (d,1H), 8.8 (bs,1H), 8.3 (dd,1H), 7.0 (d,1H), 6.0 (m,1H), 5.8 (dd,2H), 4.1 (t,2H).

Preparation of the Organosilane (8): Olefin (7) (1.09 g) was dissolved in 10 ml dichloromethane and 10 ml dimethylchlorosilane. Chloroplatinic acid (10 mg) dissolved in a minimum of 2-propanol was then added, and the mixture was heated at reflux. Progress of the reaction was monitored by disappearance of starting material in quenched reaction aliquots. (quenching solution was composed of 5 ml absolute ethanol, 5 ml triethylamine and 5 ml diethyl ether). The assay procedure consisted of removing several drops of reaction mixture, evaporating to dryness under high vacuum to remove excess dimethylchlorosilane and adding several drops of quenching solution. The mixture was then heated for several minutes on an oil bath, diluted with dichloromethane, and examined by TLC. After about three hours, TLC analysis of quenched reaction aliquots indicated complete consumption of starting material. The crude reaction mixture was evaporated and purified by flash chromatography on silica using 2% ethanol in dichloromethane as eluent to afford 0.80 g of organosilane (8) (50% yield). $^1$H NMR (CDCl$_3$)δ:9.2 (s,1H), 8.6 (bs,1H), 8.3 (d,1H), 7.0 (d,1H), 3.6 (m,2H), 3.4 (m,2H), 1.8 (m,2H), 1.2 (t,3H), 0.7 (t,2H), 0.1 (s,6H).

Bonding of the organosilane (8), and packing of the resulting stationary phase into an HPLC column followed the procedure reported for the preparation of SP 5, except that a Kügelrohr distillation apparatus was used in the bonding reaction (115° C., 1 mm Hg, 24 hours). Stationary phase recovered from the column packer was submitted for elemental analysis (C, 3.28%) which indicated a loading of 2.5×10$^{-4}$ of selector per gram of stationary phase.

PREPARATION OF SP 8

The synthetic route for SP 8, which contained a 3,5-dinitrobenzoate ester, is shown below.

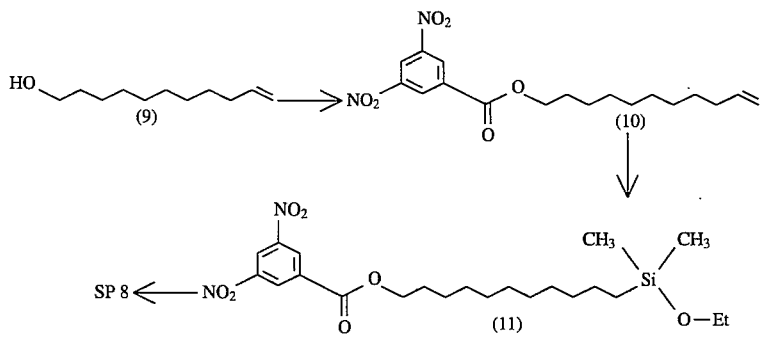

Preparation of the Olefin (10): To a cooled solution of ω-undecenylenyl alcohol ((9), 1.0 g) and triethylamine (0.65 g) in 10 mL dry tetrahydrofuran, was added 3,5-dinitrobenzoyl chloride (1.36 g) with stirring. The reaction mixture was allowed to warm to room temperature, and was then stirred for one hour. The heterogeneous solution was then diluted with ether and extracted three times with a 1.0 M HCl solution. The organic layer was washed with water, then brine, then dried over anhydrous magnesium sulfate. Filtration and evaporation yielded the olefin (10) (2.00 g, 93% yield) as a pale yellow solid. $^1$H NMR (CDCl$_3$)δ: 9.25 (d,1H), 9.2 (d,2H), 5.8 (m,1H), 4.95 (m,2H), 4.4 (t,2H), 2.05 (m,2H), 1.85 (m,2H), 0.9 (m,12H).

Preparation of the Organosilane (11): The olefin (10) was converted into ethoxysilane (11) using the hydrosilylation procedure reported for preparation of organosilane (8). Crude ethoxysilane (11) was purified by flash chromatography on silica using dichloromethane as eluent to afford 1.04 g of ethoxysilane (11) (80.6% yield) as a yellow oil. $^1$H NMR (CDCl$_3$)δ:9.25 (d,1H), 9.15 (d,2H), 4.45 (t,2H), 3.65 (q,2H), 1.85 (m,2H), 1.3 (m,16H), 0.6 (t,2H), 0.1 (s,6H).

Bonding of ethoxysilane (11) to silica, and packing of the resulting stationary phase into an HPLC column followed the procedure reported for the preparation of stationary phase SP 5 (120° C., 1 mm Hg, 24 hours). Stationary phase recovered from the column packer was submitted for elemental analysis (C, 3.94%) indicated a loading of 1.6×10$^{-4}$ moles/g.

PREPARATION OF RECOGNITION SELECTOR RS 3

The synthetic route for RS 3 is shown in Table 1 supra.

Preparation of the Triol (B): Undecylenic aldehyde (A) (50 g) and 200 g 40% formaldehyde solution were dissolved in 500 ml of a 1:1 mixture of absolute ethanol and water.

Potassium hydroxide (16.30 g) dissolved in 150 ml of a 1:1 ethanol/water mixture was then added dropwise to the stirring solution at 0° C. The reaction was allowed to warm to room temperature, stirred for four hours, then heated to 60° C. and stirred for an additional two hours at which time TLC indicated complete consumption of starting material and formation of a new product spot. The crude reaction mixture was concentrated under vacuum, then extracted several times with ether. The combined ether extracts were then washed several times with water, washed with brine, dried over anhydrous magnesium sulfate, filtered and evaporated to dryness. Flash chromatography on silica gel using 10% methanol in dichloromethane as eluent gave triol (A) (28.2 g, 41.4% yield) as a white solid. $^1$H NMR (CDCl$_3$)δ:5.85 (m,1H), 5.0 (m,2H), 3.75 (d,6H), 2.75 (t,3H), 2.05 (m,2H), 1.3 (m,12H).

Triol (B) (1.0 g) and triethylamine (1.5 g) were dissolved in 50 ml dry tetrahydrofuran and cooled in an ice bath. 3,5-dinitrobenzoyl chloride (3.0 g) was then added, and the solution was allowed to gradually warm to room temperature while stirring overnight under a nitrogen atmosphere. Precipitated triethylammonium hydrochloride was then removed by filtration, and the filtrate was washed several times with a 1M HCl solution, dried over anhydrous magnesium sulfate, filtered, and evaporated to dryness. Ether trituration of the resulting oil gave the recognition selector of the present invention, RS 3 (1.64 g, 47% yield) as a white solid. $^1$H NMR (CDCl$_3$, d$_6$DMSO)δ:9.2 (d,3H), 9.1 (d,6H), 5.75 (m,1H), 4.9 (m,2H), 4.65 (2,6H), 2.0 (m,2H), 1.8 (m,2H), 1.4 (m,10H).

Preparation of the organosilane (C): RS 3 (1.60 g) was converted into ethoxysilane (C) using the hydrosilylation procedure reported for preparation of organosilane (8). The resultant crude organosilane was purified by flash chromatography (silica, 5% acetonitrile/dichloromethane) to afford the purified organosilane (C) (1.03 g, 57.2% yield) as a yellowish solid. $^1$H NMR (CDCl$_3$)δ:9.25 (d,3H), 9.15 (d,6H), 4.6 (s,6H), 3.6 (q,2H), 1.8 (m,2H), 1.6 (m,2H), 1.3 (m,12H), 0.5 (t,2H), 0.05 (s,6H).

Preparation of Recognition Stationary Phase RSP 3: Bonding of the organosilane (C) to silica, and packing of the resulting stationary phase into an HPLC column followed the procedure reported for the preparation of stationary phase SP 5 (120° C., 1 mm Hg, 24 hours). Stationary phase recovered from the column packer was submitted for elemental analysis (C, 6.30%) which indicated a loading of 1.5×10$^{-4}$ moles of selector per gram of stationary phase.

PREPARATION OF RS 7

The synthetic route for RS 7 is shown in Table 2 supra.

Triol (B) (1.0 g) and triethylamine (2.2 g) were dissolved in 50 ml dichloromethane and cooled in an ice bath. 2,4-dinitrofluorobenzene was then added. After 30 minutes the ice bath was removed and the reaction mixture was allowed to stir overnight at room temperature under nitrogen atmosphere. The crude reaction mixture was then evaporated and purified by flash chromatography on silica gel using dichloromethane as eluent to give RS 7 (1.39 g, 44% yield) as a pale yellow foam. $^1$H NMR (CDCl$_3$)δ:8.8 (d,3H), 8.5 (dd, 3H), 7.35 (d,3H), 5.8 (m, 1H), 4.95 (m,2H), 4.5 (s,6H), 2.05 (m,2H), 1.85 (m,2H), 1.4 (m,12H).

Preparation of the Organosilane (D): RS 7 (1.39 g) was converted into ethoxysilane (D) using the hydrosilylation procedure reported for preparation of organosilane (8). The resultant crude organosilane was purified by flash chromatography on silica using 5% acetonitrile in dichloro-methane as eluent to afford 1.0 g, the purified organosilane (D) (63% yield). $^1$H NMR (CDCl$_3$)δ:8.8 (d,3H), 8.5 (dd,3H), 7.35 (d,3H), 4.45 (s,6H), 3.65 (q,2H), 1.85 (m,2H), 1.25 (m,14H), 1.2 (t,3H), 0.55 (t,2H), 0.1 (s,6H).

Preparation of Recognition Stationary Phase RSP 7: Bonding of the organosilane (D) to silica, and packing of the resulting stationary phase into an HPLC column followed the procedure reported for the preparation of stationary phase 5 (130° C., 1 mm Hg, 24 hours). Stationary phase recovered from the column packer was submitted for elemental analysis (C, 6.29%) which indicated a loading of 1.6×10$^{-4}$ moles of selector per gram of stationary phase.

RESULTS AND DISCUSSION

Evaluation of SP 1–8 and RSP 3 and RSP 7

Table 6 shows chromatographic data directed to the separation of the analytes shown in Table 3, including $C_{60}$ and $C_{70}$, on SP's 1-8 and the recognition stationary phase of the present invention exemplified by RSP 3 and RSP 7. As seen from Table 6, RSP 7 afforded the largest capacity factor (k') for buckminsterfullerene ($C_{60}$).

TABLE 6

| | Capacity Factors for Stationary Phases SP 1-8 and RSP 3 and RSP 7 | | | | | | | | | |
|---|---|---|---|---|---|---|---|---|---|---|
| Analyte | SP 1 | SP 2 | SP 3 | SP 4 | SP 5 | SP 6 | SP 7 | SP 8 | RSP 3 | RSP 7 |
| Benzene | 0.18 | 0.15 | 0.11 | 0.12 | 0.12 | 0.13 | 0.10 | 0.10 | 0.14 | 0.17 |
| Biphenyl | 0.53 | 0.35 | 0.19 | 0.17 | 0.33 | 0.34 | 0.22 | 0.19 | 0.38 | 0.44 |
| Naphthylene | 0.77 | 0.46 | 0.19 | 0.19 | 0.40 | 0.44 | 0.26 | 0.27 | 0.58 | 0.58 |
| Anthracene | 2.19 | 1.06 | 0.34 | 0.30 | 1.12 | 1.24 | 0.70 | 0.70 | 1.74 | 1.28 |
| Phenanthrene | 2.57 | 1.19 | 0.34 | 0.31 | 1.22 | 1.35 | 0.72 | 0.81 | 2.06 | 1.41 |
| 1,2-Benzanthracene | 5.55 | 2.27 | 0.57 | 0.47 | 3.00 | 3.31 | 1.97 | 1.88 | 5.61 | 3.30 |
| Pyrene | 5.96 | 2.27 | 0.43 | 0.39 | 2.53 | 2.73 | 1.49 | 2.11 | 5.84 | 2.68 |
| Chrysene | 6.30 | 2.43 | 0.60 | 0.50 | 3.23 | 3.46 | 2.09 | 2.13 | 6.45 | 3.57 |
| $C_{60}$ | 2.99 | 1.19 | 1.98 | 2.62 | 1.01 | 2.26 | 2.45 | 0.50 | 1.61 | 6.59 |
| $C_{70}$ | 4.65 | 1.90 | 4.16 | 5.31 | 1.80 | 4.76 | 7.10 | 0.80 | 3.28 | 20.77 |
| α* | 1.60 | 1.56 | 2.10 | 2.03 | 1.78 | 2.11 | 2.89 | 1.60 | 2.03 | 3.15 |

Conditions: mobile phase = 5% dichloromethane in hexane, flow rate = 2.00 mL/min., ambient temperature, Void time determined using 1,3,5-tri-t-butylbenzene.
*indicates separation factor for $C_{60}$ and $C_{70}$.

Figure 3:
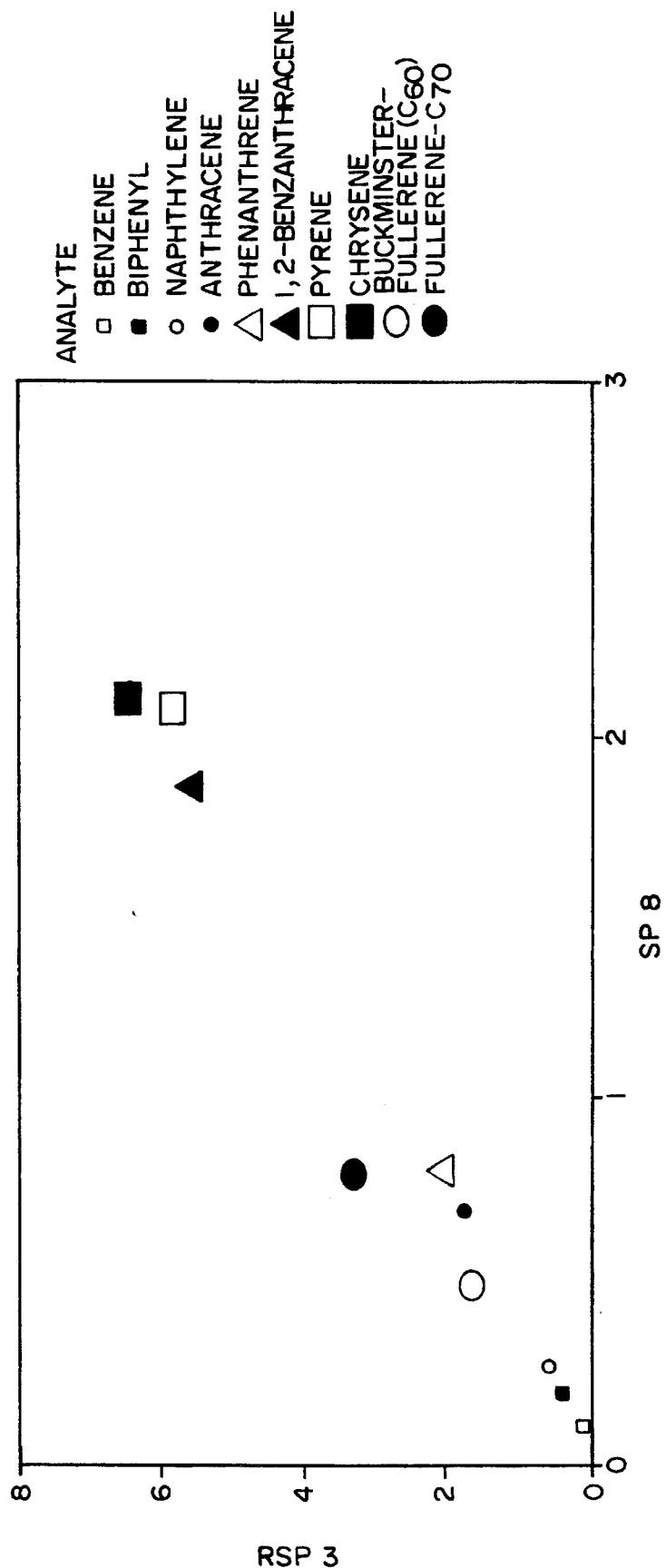
FIG. 3 is a graph showing the relative capacity factors for ten different analytes, including $C_{60}$ and $C_{70}$, using a π-acidic dinitrobenzoate ester stationary phase, SP 8, and a stationary phase formed with a recognition selector (RS 3) of the present invention.

FIG. 3 depicts the relative capacity factors of the ten analytes tested on stationary phase SP 8 and RSP 3, which was formed with the recognition selector of the present invention. As seen in FIG. 3, the best line through the data points for the polycyclic aromatic hydrocarbon analytes had a slope of 3.03. The data points for the fullerene analytes $C_{60}$ and $C_{70}$ fell only slightly above the line defined by the polycyclic aromatic hydrocarbon analytes.

Figure 4:
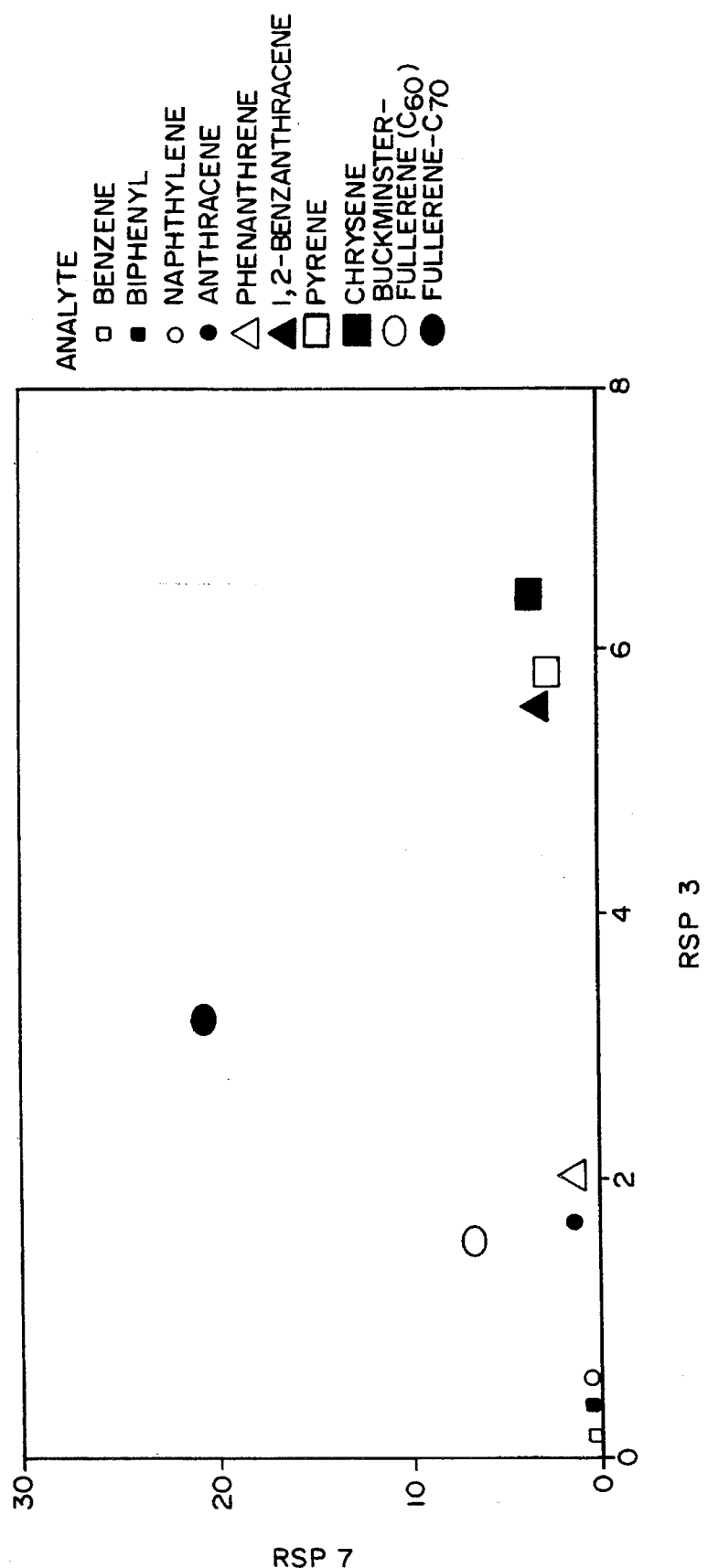
FIG. 4 is a graph showing the relative capacity factors for ten different analytes, including $C_{60}$ and $C_{70}$, using stationary phases formed with recognition selectors RS 3 and RS 7 of the present invention.

RSP 7, formed with the recognition selector of the present invention, afforded excellent retention and separation for all of the analytes. Of the stationary phases tested in Table 6, RSP 7 showed the greatest retention for the fullerenes and the best separation factor for the $C_{60}/C_{70}$ mixture. The relative capacity factors for all ten analytes on the two tripodal stationary phases of the invention that were tested, RSP 3 and RSP 7, are illustrated in FIG. 4. It is believed that the reason RSP 7 provided the degree of increased retention for the fullerenes relative to the tripodal ester RSP 3 is the positioning of the K-acidic groups in RSP 7, which is one atom closer to the branching point than in RSP 3; this could conceivably impart some degree of conformational rigidity or a more favorable geometry for simultaneous multipoint interaction to RSP 7.

What is claimed is:

1. A chiral selector having immobilized on a support or forming part of a mobile phase compound having the formula:

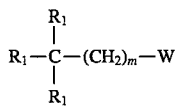

wherein $R_1$ is

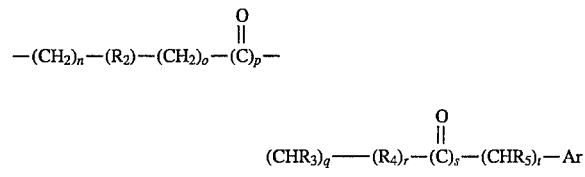

wherein $R_2$ is O, S or $NR_{12}$ wherein $R_{12}$ is independently hydrogen or P=O with the proviso that when $R_{12}$ is P=O, then only one such group is present and all $R_2$'s are additionally bonded to $R_{12}$;

$R_4$ is independently O, S or NH, $R_3$ and $R_5$ are each independently hydrogen or lower alkyl, n and o are each independently zero, 1, 2 or 3, p, q, r, s and t are each independently zero or 1, Ar is a monocyclic or ortho-fused polycyclic aromatic moiety having up to 10 carbon atoms, either of which may be unsubstituted or substituted with one or more lower alkyl, $NO_2$, $N(R_6)_3^+$, CN, $COOR_7$, $SO_3H$, $COR_8$ and $OR_9$ wherein $R_6$, $R_7$, $R_8$ and $R_9$ are each independently hydrogen or lower alkyl;

W is H or CH=$CH_2$; and m is 1 to 10.

2. The chiral selector of claim 1 wherein n and p are each 1;

o, q, r, s and t are each zero;

$R_2$ is O; and

Ar is 3,5-dinitrophenyl.

3. The chiral selector of claim 2 wherein W is CH=$CH_2$ and m is 7.

4. The chiral selector of claim 2 wherein W is hydrogen.

5. The chiral selector of claim 1 wherein n and p are each 1;

o, q, r, s and t are each zero;

$R_2$ is NH; and

Ar is 3,5-dinitrophenyl.

6. The chiral selector of claim 5 wherein W is CH=$CH_2$ and m is 7.

7. The chiral selector of claim 5 wherein W is hydrogen.

8. The chiral selector of claim 1 wherein n, o, p and r are each 1;

q, s and t are each zero;

$R_2$ is O;

$R_4$ is NH; and

Ar is 3,5-dinitrophenyl.

9. The chiral selector of claim 8 wherein W is CH=$CH_2$ and m is 7.

10. The chiral selector of claim 8 wherein W is hydrogen.

11. The chiral selector of claim 1 wherein n is 1;

o, p, q, r, s and t are each zero;

$R_2$ is O; and

Ar is 2,4-dinitrophenyl.

12. The chiral selector of claim 11 wherein W is CH=$CH_2$ and m is 7.

13. The chiral selector of claim 11 wherein W is hydrogen.

14. The compound of claim 1 wherein n, p, q, r and s are each 1;

o and t are each zero;

$R_2$ and $R_4$ are each NH;

$R_3$ is isobutyl; and

Ar is 3,5-dinitrophenyl.

15. The chiral selector of claim 14 wherein W is CH=$CH_2$ and m is 7.

16. The chiral selector of claim 14 wherein W is hydrogen.

17. The chiral selector of claim 1 wherein n, p, q and r are each 1;

o, s and t are each zero;

$R_2$ is O;

$R_3$ is $CH_3$;

$R_4$ is NH; and

Ar is β-naphthyl.

18. The chiral selector of claim 17 wherein W is CH=$CH_2$ and m is 7.

19. The chiral selector of claim 17 wherein W is hydrogen.

20. The chiral selector of claim 1 wherein n, p and q are each 1;

o, r, s and t are each zero;

$R_2$ is O;

$R_3$ is $CH_3$; and

Ar is 6-methoxy-β-naphthyl.

21. The chiral selector of claim 20 wherein W is CH=$CH_2$ and m is 7.

22. The chiral selector of claim 20 wherein W is H.

23. The chiral selector of claim 1 wherein n, o, p, r and t are each 1;

q and s are each zero;

$R_2$ is O;

$R_4$ is NH;

$R_5$ is $CH_3$; and

Ar is α-naphthyl.

24. The chiral selector of claim 23 wherein W is CH=$CH_2$ and m is 7.

25. The chiral selector of claim 23 wherein W is hydrogen.

26. The chiral selector of claim 1 wherein n and q are each 1;

o, p, r, s and t are each zero;

$R_2$ is $NR_{12}$; and

Ar is α-naphthyl.

27. The chiral selector of claim 26 wherein $R_{12}$ is P=O with the proviso that only one such P=O group is present and all $R_2$'s are additionally bonded to said P=O group.

28. The chiral selector of claim 27 wherein

N is CH=$CH_2$; and m is 7.

29. The chiral selector of claim 28 wherein W is hydrogen.

\* \* \* \* \*

UNITED STATES PATENT AND TRADEMARK OFFICE
CERTIFICATE OF CORRECTION

PATENT NO. : 5,487,831
DATED : January 30, 1996
INVENTOR(S) : William H. Pirkle, et al.

It is certified that error appears in the above-indentified patent and that said Letters Patent is hereby corrected as shown below:

In the Abstract, line 20: " $N(R_6)_3^{30}$ " should read -- $N(R_6)_3^+$ --

Column 2, lines 11 & 38: "K-acidic" should read -- $\pi$-acidic --

Column 3, delete lines 5-7.

Column 4, insert the following on line 8:

-- $-(CH_2)_n-(R_2)-(CH_2)_o-(\overset{O}{\overset{\|}{C}})_p-(CHR_3)_q-(R_4)_r-(\overset{O}{\overset{\|}{C}})_s-(CHR_5)_t-Ar,$ --

Column 6, line 57: "are each o, r," should read --are each 1; o, r,--

Column 9, insert the following on line 35: -- RSP 3 --

Column 15, line 58: "dihydroguinoline" should read --dihydroquinoline--

UNITED STATES PATENT AND TRADEMARK OFFICE
CERTIFICATE OF CORRECTION

PATENT NO. : 5,487,831
DATED : January 30, 1996
INVENTOR(S) : William H. Pirkle, et al.

It is certified that error appears in the above-indentified patent and that said Letters Patent is hereby corrected as shown below:

Column 21, line 11: "K-acidic" should read -- π-acidic --

Column 22, line 23, Claim 14: "compound of" should read --chiral selector of--

Signed and Sealed this

Tenth Day of September, 1996

Attest:

BRUCE LEHMAN

Attesting Officer

Commissioner of Patents and Trademarks